United States Patent [19]

Boeck

[11] Patent Number: 4,977,083
[45] Date of Patent: Dec. 11, 1990

[54] PROCESSES FOR PREPARING A54145 COMPOUNDS

[75] Inventor: LaVerne D. Boeck, Indianapolis, Ind.

[73] Assignee: Eli Lilly and Company, Indianapolis, Ind.

[21] Appl. No.: 179,930

[22] Filed: Apr. 11, 1988

[51] Int. Cl.$^5$ ............... C12P 21/04; A61K 37/02; C07K 7/64
[52] U.S. Cl. .................. 435/71.3; 530/317; 514/11; 435/896
[58] Field of Search ........... 435/71, 244, 896, 71.3, 435/71.2, 71.1

[56] References Cited

U.S. PATENT DOCUMENTS

| | | | |
|---|---|---|---|
| 4,208,403 | 6/1980 | Hamill et al. | 424/115 |
| 4,331,594 | 5/1982 | Hamill et al. | 530/317 |
| 4,356,265 | 10/1982 | Hatano et al. | 435/244 |
| 4,396,543 | 8/1983 | Debono | 530/323 |
| 4,399,067 | 8/1983 | Debono | 53/323 |
| 4,537,717 | 8/1985 | Abbott et al. | 530/317 |

FOREIGN PATENT DOCUMENTS

| | | | |
|---|---|---|---|
| 0178152A2 | 4/1986 | European Pat. Off. | |
| 0178152 | 4/1986 | European Pat. Off. | 435/71 |

Primary Examiner—Richard A. Schwartz
Assistant Examiner—Mary Mosher
Attorney, Agent, or Firm—Joseph A. Jones; Leroy Whitaker; Nancy J. Harrison

[57] ABSTRACT

Improved processes for preparing A54145 components and cyclic peptide derivatives (A54145 compounds) comprising: (1) feeding alkanoic or alkenoic acids or alcohols, or esters or salts thereof, (2) feeding glucose at a rate from about 6–9 g/L/day, or (3) feeding enzymatic soy digest at a rate from about 2–4 g/L/day to an A54145-producing culture during its fermentation and recovering the A54145 compound, are provided.

13 Claims, No Drawings

PROCESSES FOR PREPARING A54145 COMPOUNDS

SUMMARY OF THE INVENTION

This invention relates to improved processes for preparing A54145 components and cyclic peptide derivatives (A54145 compounds). One aspect of the invention is a process for preparing an A54145 component which comprises feeding a $C_4$–$C_{18}$-alkanoic or alkenoic acid or alcohol, or an ester or salt thereof, to an A-54145-producing culture during its fermentation and recovering the A54145 components. This process provides significantly increased product yields of A54145 components.

Another aspect of this invention is a process for preparing certain A54145 cyclic peptide derivatives which comprises feeding a $C_6$–$C_{10}$-alkanoic or alkenoic acid or alcohol, or an ester or salt thereof, to an A-54145-producing culture during its fermentation and recovering the A54145 cyclic peptide derivative. In addition to increasing product yields of the derivatives, this process has further advantages in that it: (1) requires fewer steps than the previous process and (2) requires less time.

Still another aspect of this invention is a process for preparing A54145 compounds which comprises feeding glucose at a rate of from about 6.0 to about 9.0 grams per liter per day to an A-54145-producing culture, starting from about 18 to about 24 hours after initiating the production stage, and continuing throughout its fermentation. The advantage of this process is that product yields of the A54145 compounds are increased.

This invention further provides a process for preparing A54145 compounds which comprises feeding an enzymatic soy digest at a rate of from about 2 to about 4 grams/liter/day to an A54145-producing culture, starting from about 100 to about 120 hours after initiating the production stage, and continuing throughout its fermentation. This process also provides increased product yields.

In another aspect, this invention provides a process for preparing specific A54145 compounds which comprises adding an amino acid selected from L-Val, L-Leu, L-Ile, L-Glu, L-Asp and L-Tyr to the fermentation medium and recovering the A54145 compound produced.

DETAILED DESCRIPTION OF THE INVENTION

In this specification, the following abbreviations, most of which are commonly known in the art, are used:
Ala: Alanine
Asn: Asparagine
(OH)Asn: β-hydroxy-asparagine
Asp: Aspartic acid
(MeO)Asp: β-methoxy-aspartic acid
Glu: Glutamic acid
Gly: Glycine
Ile: Isoleucine
Lys: Lysine
Thr: Threonine
Trp: Tryptophan
Sar: Sarcosine
Val: Valine
3—MG: 3-Methylglutamic acid
HPLC: High performance liquid chromatography
$^1$H NMR: Proton nuclear magnetic resonance
TLC: Thin-layer chromatography
IR: Infrared
UV: Ultraviolet
FABMS: Fast-atom-bombardment mass spectrometry The A54145 antibiotics are a new group of lipopeptide antibiotics. Each contains a cyclic peptide unit with a fatty acid side chain. LaVerne D. Boeck, David S. Fukuda, Jon S. Mynderse, Marvin M. Hoehn, Ralph E. Kastner and Harold R. Papiska describe antibiotic A54145, comprising major components A and B and minor components B, C, D, E, F and $A_1$, and its production by *Streptomyces fradiae* strains NRRL 18158, NRRL 18159 and NRRL 18160 in their copending application entitled A54145 ANTIBIOTICS AND PROCESS FOR THEIR PRODUCTION, attorney docket No. X-6612, Ser. No. 07/179,773, filed this same day. The *Streptomyces fradiae* strains NRRL 18158, NRRL 18159, and NRRL 18160 are part of the stock culture collection of the Midwest Area Northern Regional Research Center, U.S. Department of Agriculture, Agricultural Research Service, 1815 North University Street, Peoria, Ill. 61604, from which they are available to the public.

The A54145 components can be represented by general structure 1:

$$\text{NHR—Trp—Glu—(HO)Asn—Thr—Sar—Ala—Asp—Lys} \atop \phantom{xxxxxxxxxxxxxxxxxxxxxxxxxxxxxxxxx} \mid \atop \phantom{xxxxxxxxxxxxxxxxxxxxxxxxxxxxxxxxx} \text{O} \atop \phantom{xxxxxxxxxxxxxxxxxxxxxxxxxxxxxxxxx} \mid \atop \text{X—Y—Asn—Gly—(MeO)Asp} \qquad 1$$

wherein
R is selected from n-decanoyl, 8-methyldecanoyl and 8-methylnonanoyl;
X is Ile or Val; and
Y is Glu or 3—MG;
provided that: (1) when X=Val and Y=3—MG, R must be 8-methyldecanoyl; and (2) when X=Val and Y=Glu, R must be 8-methylnonanoyl.

The individual A54145 components have specific structures 1a–1h:

| Structure | Component | X | Y | R |
|---|---|---|---|---|
| 1a | A | Ile | Glue | 8-methylnonanoyl |
| 1b | B | Ile | 3-MG | n-decanoyl |
| 1c | C | Val | 3-MG | 8-methyldecanoyl |
| 1d | D | Ile | Glu | 8-methyldecanoyl |
| 1e | E | Ile | 3-MG | 8-methyldecanoyl |
| 1f | F | Val | Glu | 8-methylnonanoyl |
| 1g | $A_1$ | Ile | Glu | n-decanoyl |
| 1h | $B_1$ | Ile | 3-MG | 8-methyldecanoyl |

Process 1

One aspect of this invention is a process for preparing a formula 1 compound which comprises adding a $C_4$–$C_{18}$-alkanoic or alkenoic acid or alcohol, or an ester or salt thereof, to an A54145-producing culture, starting from about 20 to about 26 hours after initiating the production stage, and continuing throughout the fermentation to increase the yield of formula 1 compound produced. This process substantially increases the yields of specific components over those obtained using the previous process.

Process 2

In their copending application entitled "A54145 CYCLIC PEPTIDES", attorney Docket No. X-6827, Ser. No. 07/179,928, also filed this day, David S. Fukuda and Jon S. Mynderse describe their discovery that the fatty acid side chains of the A54145 antibiotics can be removed enzymatically to give the cyclic peptide unit ("nucleus"). For convenience, this cyclic peptide is called an A54145 nucleus. Thus far, they have obtained four unique A54145 nuclei. These nuclei have been designated the A54145A, A54145B, A54145C and A54145F nuclei.

The four A54145 nuclei appear to have the common structure 2 and individual structures 2a–2d:

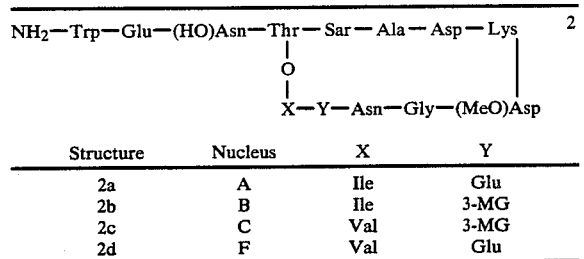

| Structure | Nucleus | X | Y |
|---|---|---|---|
| 2a | A | Ile | Glu |
| 2b | B | Ile | 3-MG |
| 2c | C | Val | 3-MG |
| 2d | F | Val | Glu |

The A54145 nuclei are useful intermediates to another group of compounds found by Fukuda and Mynderse. These compounds, which are called A54145 cyclic peptide derivatives, are described in their copending application entitled "DERIVATIVES OF A54145 CYCLIC PEPTIDES, attorney docket No. X-6848, Ser. No. 07/179,929, also filed this even date. One group of those compounds can be represented by formula 3:

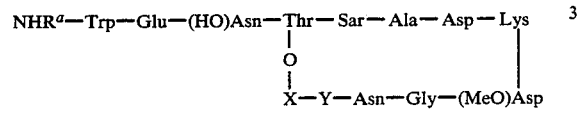

wherein:
$R^a$ is $C_6$–$C_{10}$-alkanoyl;
X is Ile or Val; and
Y is Glu or 3—MG; provided that:
(1) when X=Ile and Y=Glu or 3—MG, $R^a$ cannot be 8-methylnonanoyl, 8-methyldecanoyl or n-decanoyl;
(2) when X=Val and Y=3—MG, $R^a$ cannot be 8-methyldecanoyl; and
(3) when X=Val and Y=Glu, $R^a$ cannot be 8-methylnonanoyl.

Previously, formula 3 derivatives were prepared by a multistep process which was time-consuming, yield-consuming and expensive. This invention provides an improved process for making the formula 3 derivatives by direct biosynthesis in the initial fermentation. The prior process for preparing a formula 3 derivative, such as the n-decanoyl derivative of A54145F nucleus, required the following steps:
Producing the A54145 component by fermenting the A54145-producing culture.
  a. Initiating with a lyophilized pellet or liquid nitrogen ampoule.
  b. Primary inoculum stage (48 hours).
  c. Secondary inoculum stage (24 hours).
  d. Fermentation (144–168 hours).
2. Filtering, adsorbing on a resin, eluting and concentrating to obtain A54145.
3. Preparing the t-BOC derivative of A54145.
4. Concentrating the A54145.

5. Fermenting the deacylating culture, e.g. *Actinoplanes utahensis*.
  a. Initiating with a liquid nitrogen ampoule
  b. Primary inoculum stage (72 hours)
  c. Secondary inoculum stage (48 hours)
  d. Fermentation (67–90 hours)
6. Deacylating the t-BOC-blocked A54145 with the deacylating culture.
7. Filtering, absorbing on resin, eluting, and concentrating to give the t-BOC nuclei.
8. Chromatographic separation to give the desired t-BOC nucleus.
9. Reacylating.
10. Hydrolyzing the protecting group.
11. Purifying the desired derivative.

The second process of this invention is a process for preparing a formula 3 compound which comprises adding a $C_6$–$C_{10}$-alkanoic or alkenoic acid or alcohol, or an ester or salt thereof, to an A54145-producing culture, starting from about 20 to about 26 hours after initiating the production stage, and continuing throughout the fermentation (step 1d) to give the corresponding formula 3 compound. This process eliminates steps 3, 4, 5, 6, 7, 8, 9 and 10 of the previous process. In addition, this process substantially increases the yields of specific products over those obtained using the previous process.

In Processes 1 and 2, the alkyl portion of the alkanoic or alkenoic acid or alcohol (the substrate) used can be a straight or branched chain. The straight-chain acids or alcohols, or their esters or salts, are recommended for use in these processes because of availability and lower cost. An especially preferred substrate is n-decanoic acid and its esters and salts.

When using an alkanoic acid ester, the $C_1$–$C_4$-alkyl esters are preferred. In such an ester, the $C_1$–$C_4$-alkyl group may also be straight or branched.

Representative suitable salts of alkanoic or alkenoic acids which may be used in the processes include those formed from alkali metals and alkalineearth metals such as sodium, potassium, lithium, cesium, rubidium, barium, calcium and magnesium. Suitable amine salts include the ammonium and the primary, secondary and tertiary $C_1$–$C_4$-alkyl-ammonium and hydroxy-$C_2$–$C_4$-alkyl-ammonium salts.

For processes 1 and 2, it is preferable to add the substrate to the fermentation in the form of a sterile solution. For example, n-decanoic acid is a solid at room temperature, whereas its ethyl ester is a liquid. Thus, the ethyl ester is preferred because the acid must be dissolved in a compatible liquid, such as oleic acid or methyl oleate, for efficient feeding. Oleic acid is a particularly useful solvent for this purpose, although other solvents such as ethanol, ethyl acetate and $C_1$–$C_4$ esters of unsaturated fatty acids can be used. Those substrates which are suitably fluid at fermentation temperatures may be added directly and are, therefore, preferred.

The rate of addition of the substrate to the fermentation must be low enough to avoid producing a toxic effect on the fermentation, but high enough to increase the yield of the desired compound. Rates of addition of about 0.5 to about 4 mL per liter of fermentation broth per day can be used. A rate of from about 1.5 to about 3 mL per liter of fermentation broth per day is preferred.

The substrate is added to the growing A54145-producing culture during the production stage of the fermentation, beginning at from about 20 to about 26 hours and continuing until the fermentation is terminated. The substrate can be added by various methods. It is preferable, however, to add it by a method which best approaches a steady flow.

Process 3

The group of compounds selected from A54145 components and A54145 cyclic peptide derivatives, collectively called A54145 compounds, can be represented by general formula 4.

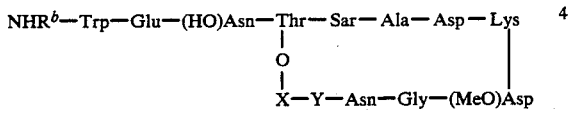

wherein
$R^b$ is $C_6$–$C_{10}$-alkanoyl
X is Ile or Val; and
Y is Glu or 3—MG.

The third aspect of this invention is a process for preparing a formula 4 compound which comprises feeding glucose at a rate from about 6 to about 9 grams/liter/day to an A54145-producing culture, starting from about 18 to about 24 hours after initiating the production stage and continuing throughout its fermentation. The improvement obtained by this process is illustrated in Table I, which compares the results obtained by standard methods with results obtained using this process.

TABLE I

Effect of Continuous Glucose Feed on A54145 Biosynthesis

| Glucose Level (%) | Glucose Addition Method | A54145 Yield (mcg/mL) |
|---|---|---|
| 4 | Included at time of medium make-up | 520 |
| 4 | Continuous feed from day 1 to day 8[a] | 1370 |

[a]Beginning 23 hours after initiating the production stage

As the results in Table I indicate, glucose feeding increases final A54145 yield by at least 150%.

When the desired formula 4 compound is an A54145 cyclic derivative, the second process must be used concomitantly to produce the appropriate derivative.

In the continuous glucose feed process, the rate of addition of the glucose must be low enough to avoid toxic affects on the fermentation, but high enough to cause a significant increase in the yield of A54145 compound. A rate of about 6 to about 9 grams/liter/day is recommended, but a rate of about 7.5 g/L/day is preferred for this process.

In this process, the glucose is added to the growing A54145-producing culture during the production stage of the fermentation. Addition should begin at from about 18 to about 24 hours after initiating the production stage and continue until the fermentation is terminated. The glucose may be added by various methods, but is preferably added as a solution, using a method which approaches a steady flow.

Process 4

In another aspect, this invention provides an improved process for preparing A54145 compounds which comprises feeding an enzymatic soy digest to the fermentation during the production stage of the fermentation. This process also provides increased product yields.

The rate of addition of the soy digest must also be low enough to avoid producing toxic effects on the fermentation, but high enough to increase the yield of the A54145 compound. Rates of addition of about 2 to about 4 grams/liter/day can be used. A rate of from about 2.5 to about 3.5 g/L/day is preferred.

As with the other processes, the substrate is added to the growing A54145-producing culture during the production stage of the fermentation beginning at from about 90 to about 120 hours and continuing until the fermentation is terminated. Although the soy digest can be added by different methods, it is preferable to add it by steady flow of a sterile solution.

The processes of this invention can be carried out over a temperature range of from about 20° to about 34° C. Temperature affects the amount of total antibiotic produced and the type of nucleus and side chain produced. Thus, the temperature of the fermentation should be adjusted appropriately in order to obtain optimum yields of the desired product. Table II summarizes temperature effects on A54145 production which were observed in fermentation studies in which only the temperature was varied.

TABLE II

EFFECT OF TEMPERATURE ON A54145 NUCLEUS AND ACYL-CHAIN BIOSYNTHESIS IN A STIRRED 165-L BIOREACTOR

| Temperature (°C.) | Total Antibiotic (mcg/mL) | Nuclei (%) | | | | Acyl Chains (%)[a] | | |
|---|---|---|---|---|---|---|---|---|
| | | A | B | C | F | $iC_{10}$ | $nC_{10}$ | $aC_{11}$ |
| 21 | 1015 | 60 | 31 | — | 9 | 79 | 15 | 6 |
| 25 | 1582 | 62 | 30 | — | 8 | 74 | 18 | 8 |
| 29 | 1623 | 39 | 51 | 3 | 6 | 64 | 21 | 14 |
| 31 | 1341 | 32 | 59 | 2 | 6 | 59 | 23 | 17 |
| 33 | 923 | 19 | 73 | 2 | 6 | 60 | 23 | 16 |

[a]$iC_{10}$ = 8-methylnonanoyl
$nC_{10}$ = n-decanoyl
$aC_{11}$ = 8-methyldecanoyl Following the fermentation, the desired A54145 compound is isolated using procedures described by Boeck, Fukuda, Mynderse, Hoehn, Kastner and Papiska in their application, discussed supra.

The A54145 compounds have antibacterial activity agents and are especially useful as growth promoting agents in animals.

The following non-limiting examples are provided to illustrate this invention. In this examples the following numbers will be used to represent specific solvent systems:

| No. | System | Ratio |
|---|---|---|
| 1 | Pyridine/HOAc/$H_2O$ | 1:1:98 |
| 2 | Pyridine/HOAc/$H_2O$/$CH_3CN$ | 1:1:88:10 |
| 2a | Pyridine/HOAc/$H_2O$/$CH_3CN$ | 1:1:87:11 |
| 2b | Pyridine/HOAc/$H_2O$/$CH_3CN$ | 1:1:86:12 |
| 2c | Pyridine/HOAc/$H_2O$/$CH_3CN$ | 1:1:83:15 |
| 2d | Pyridine/HOAc/$H_2O$/$CH_3CN$ | 1:1:82:16 |
| 2e | Pyridine/HOAc/$H_2O$/$CH_3CN$ | 1:1:78:20 |
| 2f | Pyridine/HOAc/$H_2O$/$CH_3CN$ | 1:1:73:25 |
| 2g | Pyridine/HOAc/$H_2O$/$CH_3CN$ | 1:1:70.5:27.5 |
| 2h | Pyridine/HOAc/$H_2O$/$CH_3CN$ | 1:1:68:30 |
| 2i | Pyridine/HOAc/$H_2O$/$CH_3CN$ | 1:1:67:31 |
| 2j | Pyridine/HOAc/$H_2O$/$CH_3CN$ | 1:1:66:32 |
| 2k | Pyridine/HOAc/$H_2O$/$CH_3CN$ | 1:1:65:33 |
| 2m | Pyridine/HOAc/$H_2O$/$CH_3CN$ | 1:1:63:35 |
| 3a | Pyridine/HOAc/$H_2O$/$CH_3CN$/MeOH | 1:1:70:18:10 |
| 3b | Pyridine/HOAc/$H_2O$/$CH_3CN$/MeOH | 1:1:68:20:10 |
| 3c | Pyridine/HOAc/$H_2O$/$CH_3CN$/MeOH | 1:1:63:25:10 |

-continued

| No. | System | Ratio |
|---|---|---|
| 3d | Pyridine/HOAc/H₂O/CH₃CN/MeOH | 1:1:61:27:10 |
| 3e | Pyridine/HOAc/H₂O/CH₃CN/MeOH | 1:1:58:30:10 |
| 3f | Pyridine/HOAc/H₂O/CH₃CN/MeOH | 1:1:56:32:10 |
| 3g | Pyridine/HOAc/H₂O/CH₃CN/MeOH | 1:1:53:35:10 |
| 3h | Pyridine/HOAc/H₂O/CH₃CN/MeOH | 1:1:68:25:5 |
| 3i | Pyridine/HOAc/H₂O/CH₃CN/MeOH | 1:1:73:15:10 |
| 3j | Pyridine/HOAc/H₂O/CH₃CN/MeOH | 1:1:60.5:25:12.5 |
| 3k | Pyridine/HOAc/H₂O/CH₃CN/MeOH | 1:1:71:20:7 |
| 4  | $CH_3CN/H_2O$ | 1:1 |
| 4a | $CH_3CN/H_2O$ | 15:85 |
| 5  | $CH_3OH/H_2O$ | 1:1 |

Separation of the individual antibiotic A54145 components can be followed by TLC or HPLC. One convenient analytical HPLC system is:

Analytical HPLC System for A54145 Components
Column: 4.6-mm×25-cm silica gel (Zorbax C8, Dupont)
Mobile Phase: acetonitrile/water containing 0.2% tri ethylamine and adjusted to pH 3 with phosphoric acid (35:65)
Detection: UV at 223 nm
Flow Rate: 2 mL/min A54145 components A–F have the following approximate retention times in this system:

| A54145 Factor | Retention Time (min) |
|---|---|
| A | 12.1 |
| $A_1$ | 13.1 |
| B | 14.9 |
| $B_1$ | 13.7 |
| C | 17.0 |
| D | 19.6 |
| E | 22.4 |
| F | 9.4 |

PREPARATION 1

I. Producing Antibiotic A54145 with *Streptomyces fradiae* A54145.1

A. Shake-flask Fermentation of A54145.1

The culture *Streptomyces fradiae* NRRL 18158, either as a lyophilized pellet or as a suspension maintained in liquid nitrogen, is used to inoculate 50 mL of a vegetative medium having the following composition:

| Vegetative Medium I | |
|---|---|
| Ingredient | Amount (g/L) |
| Glucose | 15.0 |
| Potato dextrin | 20.0 |
| Soybean grits | 15.0 |
| Corn steep liquor | 10.0 |
| Yeast extract | 1.0 |
| $CaCO_3$ | 5.0 |
| Tap water q.s. | 1 liter |

(Adjust the pH of the medium from ~6.1 to ~6.5 with NaOH before sterilizing; post-sterilization pH ~7)

The inoculated first-stage medium is incubated in a 250-mL Erlenmeyer flask at 30° C. for about 48 hours on a shaker orbiting in a two-inch (5.08 cm) circle at 250 rpm.

This incubated first-stage medium (1 mL) is used to inoculate 50 mL of a production medium having the following composition:

| Production Medium I | |
|---|---|
| Ingredient | Amount (g/L) |
| Glucose | 45 |
| Soybean grits | 35 |
| Blackstrap molasses | 3 |
| $CaCO_3$ | 2.5 |
| Tap water q.s. | 1 liter |

(Presterilization pH ~6.9; post-sterilization pH ~6.8)

The inoculated production medium is incubated in a 250-mL wide-mouth Erlenmeyer flask at 25° C. for 6 to 7 days on a shaker orbiting in a two-inch circle at 250 rpm.

B. Tank Fermentation of A54145.1

In order to provide a larger volume of inoculum, 10 mL of incubated vegetative medium, prepared as described in Section A, is used to inoculate 400 mL of a second-stage growth medium having the same composition as that of the first-stage vegetative medium. This second-stage vegetative medium is incubated in a two-liter wide-mouth Erlenmeyer flask for about 24 hours at 30° C. on a shaker orbiting in a two-inch circle at 250 rpm.

Incubated second-stage vegetative medium (800 mL) thus prepared is used to inoculate 115 liters of sterile production medium, prepared as described in Section A, except that 0.2 g/L of a silicone antifoam such as Sag-471 (Union Carbide) is added. The inoculated production medium is allowed to ferment in a 165-liter stirred fermentation tank for 6 to 7 days at a temperature of 25° C. Low airflow (0.25 v/v/m) and low rpm (200–300) in the stirred vessel maintain a dissolved oxygen level above 30% of air saturation. The pH is not allowed to rise above 7.5.

II. Producing Antibiotic A54145 with *Streptomyces fradiae* A54145.2

A. Shake-flask Fermentation of A54145.2

Shake-flask fermentation is carried out as in Part I, Section A, with the following exceptions:
(1) the culture is Streptomyces fradiae NRRL 18159;
(2) the vegetative medium has the following composition:

| Vegetative Medium II | |
|---|---|
| Ingredient | Amount (g/L) |
| Glucose | 10 |
| Potato starch | 30 |
| Soybean flour | 20 |
| Defatted cottonseed flour | 20 |
| $CaCO_3$ | 2 |
| Tap water | 1 liter |

(3) the vegetative medium is incubated at 25° C.; and
(4) the production medium has the following composition:

| Production Medium II | |
|---|---|
| Ingredient | Amount (g/L) |
| Glucose | 25.0 |
| Soybean grits | 18.75 |
| Blackstrap molasses | 3.75 |
| Casein | 1.25 |
| $CaCO_3$ | 3.125 |
| Sodium acetate | 8.0 |

| Production Medium II | |
|---|---|
| Ingredient | Amount (g/L) |
| Tap water q.s. to | 1 L |

(Pre-sterilization pH ~6.9; post-sterilization pH ~6.8)

B. Tank Fermentation of A54145.2

Incubated vegetative medium prepared as described in Section A is used, and the procedures of Part I, Section B, are followed with these exceptions:
(1) the amount of incubated vegetative medium used to inoculate the second-stage growth medium is 8 mL;
(2) the amount of second-stage medium used to inoculate the production medium is 2 L;
(3) the air flow is 0.125 v/v/m; and
(4) the pH is allowed to rise above 7.5.

III. Producing Antibiotic A54145 with *Streptomyces fradiae* A54145.3

The procedures of Part II, Section B, are followed except that the culture used is *Streptomyces fradiae* NRRL 18160, dissolved oxygen is controlled at 40% of air saturation, pH is controlled at 7.0 and the production medium has the following composition:

| Production Medium III | |
|---|---|
| Ingredient | Amount (g/L) |
| Soybean flour | 20.0 |
| Glucose | 5.0 |
| Blackstrap molasses | 2.5 |
| $Fe(SO_4).(NH_4)_2SO_4.6H_2O$ | 0.6 |
| Silicon defoamer | 0.2 |
| Polypropylene glycol (M.W. 2000) | 0.1 |
| Tap water q.s. to | 1 liter |

IV. Isolating Antibiotic A54145

Procedure A: Whole fermentation broth from two 100-L tanks (217 L), prepared as described in Part II, was filtered through a filter press with 3% filter aid (Hyflo Super-Cel, Manville Products, Lompoc Calif.). The filtrate (185 L) was adjusted to pH 6.4, using 5 N HCl. Diaion HP-20 resin (20 L) was added to the filtrate. The initial effluent (85 L) and a water wash (60 L) were discarded. The resin was then eluted as follows:

| Eluate | Solvent No. | Amount |
|---|---|---|
| 1 | 4a | 40 L |
| 2 | 4 | 30 L |
| 3 | 4 | 30 L |

Eluate 1 was discarded.

Eluates 2 and 3 were combined and chromatographed on 2 L of IRA-68(OAc⁻) (2.5"×32"). The initial effluent (60 L), a wash with Solvent No. 4 (10 L) and an eluate with 0.1 N HOAc:$CH_3CN$ (1:1, 10 L) were discarded. The column was then eluted with 14 L of 1.0 N HOAc:$CH_3CN$ (1:1). This fraction was concentrated under vacuum and lyophilized to give 101.1 g of antibiotic A54145.

Procedure B: Whole fermentation broth from a large tank (4600 L), prepared as described in Part II, was adjusted to pH 6.5 with HCl and filtered through a filter press with the aid of 4% Celite 545 to give 4600 L of filtrate having a pH of 6.3.

The filtrate was absorbed batch-wise onto Diaion HP-20 resin (200 L), adjusted to pH 6.0 and maintained at this pH while stirring for 2 hours. The mixture was filtered, and the filtrate was discarded.

The saturated HP-20 resin was transferred to a small tank with a welded membrane. The resin was washed first with water (800 L), agitating for 35 minutes, and then with Solvent No. 4a (400 L), agitating for 3 minutes. These washes were discarded. The resin was then eluted twice with Solvent No. 4 (600 L), agitating for 35 minutes.

The eluates were combined (1200 L) and chromatographed on an IRA-68 resin column (100 L), equilibrated in Solvent No. 4 and washed with this solvent (500 L). The column was then eluted with $CH_3CN$:0.2 N HOAc (1:1), discarding the first fractions (300 L) and combining, concentrating and lyophilizing subsequent fractions (750 L) to give 3.65 kg of antibiotic A54145.

V. Separating A54145B, A54145C, A54145D and A54145E

Antibiotic A54145 (60 g), obtained as described in Part IV, was subjected to preparative HPLC using a Chromatospac 100, 4-L Quantum LP-1/C18 silica-gel column (3"×39"). The antibiotic was dissolved in Solvent No. 1 and added to the column. Elution was monitored by UV at 280 nm.

Fractions were combined based on analytical HPLC as described supra, but detecting at 289 nm and 223 nm and collecting 500-mL fractions at a flow rate of 100 mL/min. The column was eluted as follows:

| Solvent | Fractions |
|---|---|
| 1 | 1–8 |
| 3b | 9–29 |
| 3c | 30–73 |
| 3d | 74–161 |
| 4 | 8-L strip |

On the basis of the analytical HPLC results, fractions 114–161 were combined to give a total of 8.5 g of antibiotic A54145 enriched with components B, C, D and E. This material was rechromatographed on a Chromatospac column, repeating the previous conditions, but detecting at 223 nm and using the following solvents:

| Solvent | Fractions |
|---|---|
| 1 | 1–8 |
| 3c | 9–41 |
| 3f | 42–60 |
| 3h | 61–83 |
| 4 | 8-L strip |

From this column, fractions 76–78 gave 1.75 g of A54145B-enriched material, fractions 79–83 gave 1.02 g of A54145C-enriched material, and the strip fraction gave 0.8 g of A54145D-enriched material.

VI. Separating A54145 Enriched with A54145A, A54145C and A54145F

A54145 (60 g), obtained as described in Part IV, Procedure B, was chromatographed as in Part V, but using the following solvents:

| Solvent | Fractions |
|---|---|
| 1 | 1–8 |
| 3c | 9–102 |
| 4 | 103–122 |

Fractions were combined on the basis of analytical HPLC to give 2.54 g of A54145F-enriched material, 5.1 g of A54145A-enriched material and 10.56 g of A54145C-enriched material.

PREPARATION 2

Isolating A54145A

A54145A-enriched material (1 g), obtained as described in Preparation 1, was purified, using the following preparative HPLC system: two 1"×12" stainless steel columns packed with Zorbax ODS (12 μ) in series.
Detection: UV at 280 nm
Flow Rate: 9 mL/minute The material was dissolved in Solvent No. 1 for injection onto the column. The column was eluted as follows:

| Solvent | Fractions[a] |
|---|---|
| 1 | 1–18 |
| 3a | 19–145 |
| 4 | 146–165 |

[a]Fraction volume = 18 mL

Fractions containing A54145A (fractions 86–96) were combined, concentrated under vacuum and lyophilized to give 212 mg of purified A54145A.

Characteristics of A54145A
Mol. Wt.: 1643
Mol Formula $C_{72}H_{109}N_{17}O_{27}$
High Resolution FABMS(M+H): Found: 1644.7778, Calcd. for $C_{72}H_{110}N_{17}O_{27}$: 1644.7757.
UV (EtOH) λmax: 219 nm (ε 35,000), 280 (ε 5,250), shoulder 288 (ε 4,600).
IR (KBr): essentially the same as that of A54145B, infra
Optical Rotation: $[\alpha]_{589}^{25°\,C.}$ No Rotation (CH$_3$OH), $[\alpha]_{365}^{25°\,C.}$ −14.0° (c 0.1, CH$_3$OH).
Amino-acid Analysis: Asp 973(2), Thr 441(1), Glu 1056(2), Gly 528(1), Ala 549(1), Ile 469(1), Trp 465(1)

PREPARATION 3

Isolating A54145B

The A54145B-enriched material obtained in Preparation 1 (500 mg) was chromatographed using the procedure of Preparation 2. The column was eluted as follows:

| Solvent No. | Fractions[a] |
|---|---|
| 1 | 1–16 |
| 3g | 17–95 |
| 5 | 96–115 |

[a]Fraction volume = 18 mL

Fractions containing A54145B (fractions 64–70) were combined, concentrated under vacuum and lyophilized to give 330 mg of purified A54145B.

Characteristics of A54145B
Mol. Wt.: 1657
Mol. Formula: $C_{73}H_{111}N_{17}O_{27}$
High Resolution FABMS(M+H): Found: 1658.7954, Calcd. for $C_{73}H_{112}N_{17}O_{27}$: 1658.7914
UV (EtOH) λmax: 220 nm (ε 41,854), 281 (ε 5,613), 289 (ε 5,084)
IR (KBr): ranging from 3335 to 3313; 2930, 1660, 1531, 1407, 1255 cm$^{-1}$
Optical Rotation: $[\alpha]_{589}^{25°\,C.}$ = −8.55° (c 0.47, H$_2$O), $[\alpha]_{365}^{25°\,C.}$ = −36.32° (c 047, H$_2$O).
Amino-acid Analysis: Asp 1039(2), Thr 466(1), Glu 564(1), Gly 528(1), Ala 525(1), Ile 491(1), Lys 514(1), Trp 491(1), 3-Me-Glu 512(1).

PREPARATION 4

Isolating A54145C

A54145C-enriched material (11.76 g), obtained as described in Preparation 1, was purified using the following preparative HPLC system:
Column: 2"−×60-cm stainless steel
Packing: Quantum LP-1/C18 silica gel (20 mμ)
Detection: UV at 280 nm
Flow Rate: 18 mL/min The material was dissolved in pyridine/HOAc/H$_2$O (1:1:98, 37 mL) for application to the column. The column was eluted as follows:

| Solvent No. | Fractions[a] |
|---|---|
| 1 | 1–10 |
| 3e | 11–160 |
| 3h | 161–550 |
| 4 | 551–582 |

[a]Fraction volume = 18 mL

Fractions containing A54145C were combined (fractions 320–331, 817.8 mg). This material (800 mg) was further purified by HPLC using a 1"×20" stainlesssteel column packed with Quantum LP-1/C18 (20 mμ) silica gel column, detection as in Preparation 7, and applying the material in pyridine/HOAc/H$_2$O (1:1:98, 15 mL). The column was eluted at a flow rate of 8 mL/min as follows:

| Solvent No. | Fractions[a] |
|---|---|
| 1 | 1–18 |
| 3f | 19–69 |
| 3g | 70–114 |
| 5 | 115–137 |

[a]Fraction volume = 16 mL

Fractions containing A54145C (fractions 84–86 and 92–98) were combined, concentrated and lyophilized to give 350 mg of C-enriched material.

This process was repeated with some variation in the solvents used, i.e., varying the amount of CH$_3$CN in the solvent and sometimes eliminating methanol in the solvent mixture, to give an additional 27.6 mg of purified A54145C.

Characteristics of A54145C
Mol. wt.: 1657
Mol. Formula: $C_{73}H_{111}N_{17}O_{27}$
High Resolution FABMS(M+H): Found: 1658.7905, Calcd. for $C_{73}H_{112}N_{17}O_{27}$: 1658.7914
UV (EtOH) λmax: 219 nm (ε 29,500), 281 (ε 4,200), 288 (ε 3,600)
IR (KBr): essentially the same as that of A54145B, supra;

Amino-acid Analysis: Asp 934(2), Thr 414(1), Glu 594(1), Gly 501(1), Ala 459(1), Val 359(1), Lys 45(1), 3—MG 487(1), Trp 308(1).

PREPARATION 5

Isolating A54145D

A54145D-enriched material (750 mg), obtained as described in Preparation 1, was purified using the preparative HPLC system described in Preparation 2, except that only one column was used. The material was applied to the column in 25 mL of the solvent, and the column was eluted at a flow rate of 7.5 mL/min as follows:

| Solvent No. | Fractions[a] |
|---|---|
| 1 | 1-6 |
| 3g | 7-89 |
| 2k | 90-101 |
| 4 | 102-115 |

[a]Fraction volume = 15 mL

Fractions containing A54145D (19-22) were combined, concentrated and lyophilized to give 219 mg of material further enriched with A54145D.

This material was purified by a second HPLC column, using the same conditions except that 5% methanol was added to solvent 4 and solvent 2k was eliminated.

The fractions from this column containing A54145D (fractions 72-74) were combined, concentrated and lyophilized to give 70 mg of purified A54145D.

Characteristics of A54145D
Mol. Wt.: 1657
Mol. Formula: $C_{73}H_{111}N_{17}O_{27}$
High Resolution FABMS(M+H): Found: 1658.7913, Calcd. for $C_{73}H_{112}N_{17}O_{27}$: 1658.7913,
UV (EtOH) λmax: 219 nm ($\epsilon$ 37,500), 280 ($\epsilon$ 5,040), 289 ($\epsilon$ 4,500)
IR (KBr): essentially the same as that of A54145B, supra;
Amino-acid Analysis: Asp 1011(2), Thr 427(1), Glu 967(2), Gly 515(1), Ala 487(1), Ile 434(1), Lys 543(1), Trp 577(1)

PREPARATION 6

Isolating A54145E

A54145E-enriched material (1.0 g), obtained as described in Preparation 1, was purified using a preparative HPLC system as in Preparation 4, but using a 1"×20" column. The material was applied in 15 mL of solvent, and the column was eluted at a flow rate of 9 mL/min as follows:

| Solvent No. | Fractions[a] |
|---|---|
| 1 | 1-19 |
| 2h | 20-118 |
| 2j | 119-215 |
| 4 | 216-225 |

[a]Fraction volume = 18 mL

Fractions containing A54145E (fractions 147-160) were combined, concentrated and lyophilized to give 49.7 mg of material further enriched with A54145E.

This material was purified using two 9.4—×250-mm Zorbax ODS (5μ) columns in series, detecting by UV at 280 nm. The material was applied to the column in 3 mL of solvent 1, and the column was eluted at a flow rate of 3.25 mL/min as follows:

| Solvent No. | Fractions[a] |
|---|---|
| 1 | 1-12 |
| 2i | 13-180 |
| 4 | 181-193 |

[a]Fraction volume = 6.5 mL

Fractions containing A54145E (fractions 143-160) were combined, concentrated and lyophilized to give 16.07 mg of purified A54145E.

Characteristics of A54145E
Mol. Wt.: 1671
Mol. Formula: $C_{74}H_{113}N_{17}O_{27}$
High Resolution FABMS(M+H): Found: 1672.8065, Calcd for $C_{74}H_{114}N_{17}O_{27}$: 1672.8069
UV (EtOH) λmax: 221 nm ($\epsilon$ 29,714), 278 ($\epsilon$ 4577), 289 (4044)
IR (KBr): essentially the same as that of A54145B, supra
Amino-acid Analysis: Asp 826(2), Thr 367(1), Glu 494(1), Gly 437(1), Ala 422(1), Ile 378(1), Lys 410(1), Trp 387(1), 3—MG 437(1)

PREPARATION 7

Isolating A54145F

A54145F-enriched material (800 mg), obtained as described in Preparation 1, was purified using an HPLC system as in Preparation 4, but with a 1"×20" column. The material was applied to the column in 10 mL of solvent 1, and the column was eluted at a flow rate of 8 mL/min as follows:

| Solvent No. | Fractions[a] |
|---|---|
| 1 | 1-10 |
| 2f | 11-60 |
| 2g | 61-99 |
| 2k | 100-134 |
| 4 | 135-150 |

[a]Fraction volume = 16 mL

Fractions containing A54145F (fractions 120-128) were combined, concentrated and lyophilized to give 366.2 mg of purified A54145F.

Characteristics of A54145F
Mol. Wt.: 1629
Mol Formula: $C_{71}H_{107}N_{17}O_{27}$
High Resolution FABMS(M+H): Found: 1630.7634, Calcd. for $C_{71}H_{108}N_{17}O_{27}$: 1630.7601
UV (EtOH) λmax: 219 nm ($\epsilon$ 36,750), 280 ($\epsilon$, 5,100), 288 ($\epsilon$ 4,450)
IR (KBr): essentially the same as that of A54145B, supra
Optical Rotation $[\alpha]_{589}^{25° C.} = -3.0°$ (c 1.0, $H_2O$), $[\alpha]_{365}^{25° C.} = -6.0°$ (c 1.0, $H_2O$).
Amino-acid Analysis: Asp 959(2), Thr 428(1), Glu 965(2), Gly 494(1), Ala 487(1), Val 363(1), Lys 492(1), Trp 452(1).

PREPARATION 8

Isolating $A54145A_1$
Procedure A:

$A54145A_1$-enriched material was obtained using the following procedure: Whole broth (103 L), prepared as described in Preparation 1, Part II, was treated as described in Preparation 1, Part IV, Procedure A, except that instead of the IRA-68(OAc⁻) column, the combined eluates were chromatographed over a 40—×780-mm BioRex 5 (Cl⁻) column, using gradient elution with a 0.1 N–1.0 N NaCl solvent system and collecting 100-mL fractions.

Fractions containing A54145 were combined and desalted over a 40—×400-mm HP-20 column, again collecting 100-mL fractions. Fractions containing A54145 were combined and lyophilized to give 12.08 g of antibiotic A54145.

A portion of this antibiotic A54145 (2 g) is subjected to preparative HPLC using a Waters PrepPak 500 (C18) column, using a linear gradient of water to $H_2O:CH_3CN(1:1)$ containing 1% $NH_4H_2PO_4$. Fractions containing $A54145A_1$ are collected and desalted over an HP-20 column, eluting with Solvent 4.

This step is repeated twice, and the $A_1$-enriched material is combined (937 mg).

The $A_1$-enriched material is chromatographed over two 1"×12" Zorbax ODS columns in series as described in Preparation 7. Fractions containing $A54145A_1$ are eluted with Solvent 2j, combined, concentrated and lyophilized to give crude $A54145A_1$ (109 mg).

This material is further purified by repeating this step to give more purified $A54145A_1$ (69.29 mg).

This material is even further purified by repeating this procedure three times, using Solvents 3j, 3h and 3k, respectively. The product obtained is desalted over HP-20 to give purified $A54145A_1$ (12.21 mg).

Procedure B:

Whole fermentation broth (160 L) is prepared as described in Preparation 17. With this procedure, the fermentation volume increases with time; therefore, beginning at 138 hours, 10-L aliquots are removed at intervals and frozen. By harvest (287 hours), a total of 50 L is removed and frozen. The frozen broth is added back to the fermentation at harvest. The whole broth is filtered with a filter aid or separated using a centrifuge. A portion of the filtrate (55 L) is worked up using the procedure of Preparation 14. Fractions containing $A54145A_1$ are eluted with solvent 4, concentrated and freeze-dried. Following this procedure gave 111.3 g of $A54145A_1$-enriched material.

This material is chromagraphed over a 1"×16" Zorbax C8 (12μ) column. The column is eluted with solvent 2h. Following this procedure gave 374 mg of further $A54145A_1$-enriched material, which contained approximately 46% $A54145A_1$, 19% $A54145B_1$, 14% A54145A, 13% A54145B and 8% of an unidentified material (HPLC analysis).

Preparative HPLC using appropriate solvents is carried out on the further purified material to obtain $A54145A_1$ in pure form.

Characteristics of $A54145A_1$

Mol. Wt.: 1643

Mol. Formula: $C_{72}H_{109}N_{17}O_{27}$

High Resolution FABMS(M+H): Found: 1644.7691, Calcd. for $C_{72}H_{110}N_{17}O_{27}$: 1644.7757

UV (EtOH) $\lambda$max: 220 nm ($\epsilon$ 41,623), 281 ($\epsilon$ 5,750), 289 ($\epsilon$ 4,950)

Optical Rotation $[\alpha]_{589}^{25°\ C.}$ —10.4° (c 0.69, $CH_3OH$).

Amino-acid Analysis: Asp 1209(2), Thr 554(1), Glu 1209(2), Gly 636(1), Ala 617(1), Ile 576(1), Lys 604(1), Trp 514(1).

PREPARATION 14

Isolating $A54145B_1$

Whole fermentation broth (100 L), prepared as described in Preparation 3, was worked up as described in Preparation 4, Procedure A, except that chromatography on IRA-68 was omitted. The material was eluted with solvent 4a, concentrated and freeze-dried to give 248.2 g of crude antibiotic A54145.

A portion of this material (60 g) was chromatographed on a 2"×60-cm LP-1/C18 silica gel column.

Detection: UV at 254 and 280 mm.

Flow Rate: 25 mL/minute/fraction.

The column was eluted as follows:

| Solvent No. | Fractions |
|---|---|
| 1 | 1–138 |
| 2f | 139–411 |
| 2h | 412–560 |
| 2m | 561–976 |
| 4 | 977–1000 |

Fractions containing A54145B and $A54145B_1$ were pooled and concentrated as follows:

| Pool | Fraction | Weight (g) |
|---|---|---|
| 1 | 951–1000 | 1.10 |
| 2 | 635–667 | 4.62 |
| 3 | 685–719 | 3.95 |

The A54145B and $A54145B_1$-enriched fractions (Pools 2-3) were further purified over two 1"×12" Amicon C18 columns.

Detection: UV at 280 mm.

Flow Rate: 20 mL/1.6 minute/fraction.

The columns were eluted with pyridine/HOAc/$H_2O/CH_3CN$ (0.1/0.1/67.3/32.5). Fractions containing A54145B were combined to give 554 mg of A54145B, and fractions containing $A54145B_1$ were combined to give mg of purified $A54145B_1$.

Other A54145B-enriched fractions (Pool 1) were also purified in this manner to give an additional 394.5 mg of A54145B.

Characteristics of $A54145B_1$

Mol. Wt.: 1657

Mol. Formula: $C_{73}H_{111}N_{17}O_{27}$

High Resolution FABMS(M+H): Found: 1658.7911 Calcd. for $C_{73}H_{112}N_{17}O_{27}$: 1658.7914

UV (EtOH) $\lambda_{max}$: 221 nm ($\epsilon$ 39,100), 282 ($\epsilon$, 5,500), 290 ($\epsilon$ 4,740), IR (KBr): essentially the same as that of A54145B, supra.

Amino-acid Analysis: Asp 935(2), Thr 422(1), Glu 556(1), Gly 480(1), Ala 434(1), Ile 438(1), Lys 467(1), Trp 440(1), 3—MG 426(1).

EXAMPLE 1

Effect of Lipid Precursors, Media and Feeding Enzymatic Soy Digest on A54145 Production A54145 fermentations were carried out as in Preparation 1, Section III, using the following three production media, with and without lipid feeding:

| Medium A | |
|---|---|
| Ingredient | Amount (g/L) |
| Glucose | 25.0 |
| Soybean grits | 15.0 |
| Blackstrap molasses | 3.0 |
| Acid-hydrolyzed casein | 1.0 |
| $CaCO_3$ | 2.5 |
| Tap Water | q.s. 1 liter |

(Pre-sterilization pH~7.0; post-sterilization pH~7.1)

| Medium B | |
|---|---|
| Ingredient | Amount (g/L) |
| Soybean flour | 20.00 |
| Glucose | 5.0 |
| Blackstrap molasses | 2.5 |
| $Fe(SO_4).(NH_4)_2SO_4.6H_2O$ | 0.6 |
| Silicon defoamer | 0.2 |
| Polypropylene glycol (M.W 2000) | 0.1 |
| Potato dextrin | 30.0 |
| Tap water | q.s. to 1 liter |

| Medium C | |
|---|---|
| Ingredient | Amount (g/L) |
| Soybean flour | 20.00 |
| Glucose | 5.0 |
| Blackstrap molasses | 2.5 |
| $Fe(SO_4).(NH_4)_2SO_4.6H_2O$ | 0.6 |
| Silicon defoamer | 0.2 |
| Polypropylene glycol (M.W 2000) | 0.1 |
| Tap water | q.s. to 1 liter |

Medium D

Medium C with an enzymatic-soy-digest (Hy Soy, Sheffield Products, Norwich New York) feeding.

Table III summarizes the results of these studies.

TABLE III

EFFECT OF LIPID PRECURSORS AND MEDIA ON YIELDS AND FACTOR SIDE CHAINS OF A54145 IN A STIRRED 165-L BIOREACTOR

| Medium | Lipid Precursor[a] | Total Antibiotic (mcg/mL) | Factor Side Chains (%)[b] | | |
|---|---|---|---|---|---|
| | | | $iC_{10}$ | $nC_{10}$ | $aC_{11}$ |
| A | — | 97 | 68 | 20 | 12 |
| A | $nC_{10}$ | 179 | 20 | 79 | 1 |
| B | — | 570 | 70 | 17 | 13 |
| B | $nC_{10}$ | 1046 | 7 | 91 | 2 |
| C | — | 1100 | 76 | 14 | 10 |
| C | $nC_{10}/C_{18:1}$ | 2316 | 19 | 74 | 7 |
| D | $nC_{10}/C_{18:1}$ | 3570 | 21 | 71 | 8 |

[a] $nC_{10}$ = ethyl caprate
$nC_{10}/C_{18:1}$ = n-decanoic acid in methyl oleate (1:1)
[b] $iC_{10}$ = 8-methylnonanoyl
$nC_{10}$ = n-decanoyl
$aC_{11}$ = 8-methyldecanoyl

EXAMPLE 2

Effect of Amino-Acid Enrichment on A54145 Production

A54145 fermentations were carried out as in Preparation 1, Section II (A), but using the culture used in Section III and the following medium:

| Ingredient | Amount (g/L) |
|---|---|
| Glucose | 30.00 |
| Soybean flour | 25.0 |
| Blackstrap molasses | 5.0 |
| $CaCO_3$ | 4.0 |
| $Fe(SO_4).(NH_4)_2SO_4.6H_2O$ | 0.6 |
| Tap water | q.s. 1 liter |

Different amino acids were added to study their effects on the A54145 nuclei and acyl side chains produced. Table IV summarizes the results of these studies.

TABLE IV

EFFECT OF AMINO ACID ENRICHMENT ON BIOSYNTHESIS OF A54145 NUCLEI AND ACYL CHAINS IN SHAKEN FLASKS

| Amino Acid | Level (M) | Total Antibiotic (%) | Nuclei[a] | | | | Acyl Chains[a,b] | | |
|---|---|---|---|---|---|---|---|---|---|
| | | | A | B | C | F | $iC_{10}$ | $nC_{10}$ | $aC_{11}$ |
| — | — | 100[c] | 50 | 39 | 1 | 10 | 65 | 18 | 17 |
| L-Val | .03 | 32 | 32 | 20 | 2 | 54 | 98 | 0 | 2 |
| L-Leu | .02 | 56 | 42 | 40 | 2 | 16 | 76 | 7 | 17 |
| L-Ile | .04 | 73 | 48 | 47 | 2 | 0 | 16 | 18 | 66 |
| L-Glu | .02 | 85 | 49 | 39 | 1 | 11 | 63 | 20 | 16 |
| L-Asp | .005 | 134 | 56 | 34 | 1 | 10 | 64 | 19 | 17 |
| L-Tyr | .02 | 59 | 12 | 76 | 1 | 11 | 67 | 18 | 15 |

[a] Percent of total produced
[b] $iC_{10}$ = 8-methylnonanoyl
$nC_{10}$ = n-decanoyl
$aC_{11}$ = 8-methyldecanoyl
[c] 550 mcg/mL Table V summarizes the results of a similar study of the effect L-tyrosine has on A54145 production. This study was made in a 115-liter fermentation run.

TABLE V

EFFECT OF L-TYROSINE ENRICHMENT ON BIOSYNTHESIS OF A54145 NUCLEI IN A STIRRED 165-L BIOREACTOR

| Amino Acid | Level (M) | Total Antibiotic (%) | Nuclei[a] | | | | Acyl Chains[a,b] | | |
|---|---|---|---|---|---|---|---|---|---|
| | | | A | B | C | F | $iC_{10}$ | $nC_{10}$ | $aC_{11}$ |
| — | — | 100[c] | 19 | 78 | 1 | 2 | 19 | 74 | 7 |
| L-Tyr | 0.01 | 102 | 10 | 87 | 1 | 1 | 28 | 67 | 5 |

[a] Percent of total produced
[b] $iC_{10}$ = 8-methylnonanoyl
$nC_{10}$ = n-decanoyl
$aC_{11}$ = 8-methyldecanoyl
[c] 3200 mcg/mL Comparing the results in Tables IV and V shows that the scale of the fermentation affects the amount of (a) total antibiotic produced, (b) nuclei produced and (c) acyl side chains produced. Adding L-tyrosine decreased total antibiotic production in the shaken-flask fermentation, but did not adversely affect production in the tank fermentation. The unsupplemented shaken-flask fermentation produced more A nucleus and more $iC_{10}$ side chain product, whereas the unsupplemented tank fermentation produced more B nucleus and more $nC_{10}$ side chain. L-tyrosine increased the percentage of B-nucleus produced in both shaken flasks and tanks, but the effect was more pronounced in flasks.

Adding L-valine or L-leucine increased the percentage of F nucleus produced and the percentage of $iC_{10}$ side chain product. This effect was more pronounced with L-valine.

Adding L-isoleucine increased the percentage of both B nucleus and $aC_{11}$ side chain produced.

EXAMPLE 3

An A54145 fermentation was carried out as described in Preparation 1, using the Part III procedure except that the following production medium was used:

| Ingredient | Amount (g/L) |
|---|---|
| Soybean flour | 30.0 |
| Blackstrap molasses | 5.0 |
| Glucose | 3.0 |
| Fe(SO$_4$).(NH$_4$)$_2$SO$_4$.6H$_2$O | 0.6 |
| Deionized Water | q.s. 1 liter |

Antifoam agents were added, and the pH was adjusted from ~6.2 to ~7.2 with 5 N NaOH.

Beginning about 23 hours after the fermentation was initiated, glucose was fed to the fermentation at a rate of approximately 6.5 g/L/day. Beginning at about 25 hours after the fermentation was initiated, a sterile solution consisting of decanoic acid and oleic acid (1:1, v/v) was fed to the fermentation at a rate of approximately 6.0 mL/L/day.

At about 117 hours after the fermentation was initiated, a feeding of enzymatic soy digest was initiated and continued at a rate of about 3.0 g/L/day.

The yield of A54145 from the fermentation after about 280 hours was 3969 mcg/mL. This yield is substantially greater than the yield of about 500 mcg/mL ordinarily obtained using similar conditions, but without the glucose, enzymatic soy digest and decanoic acid feeds used in this fermentation.

EXAMPLE 4

Another series of fermentations was carried out using the procedures of Example 1 with Medium C, but adding different C$_4$-C$_{18}$-alkanoic acids and esters to enhance A54145 production. The results of these studies are shown in Table VI.

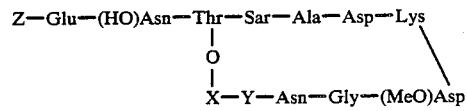

wherein Z is a group of formula

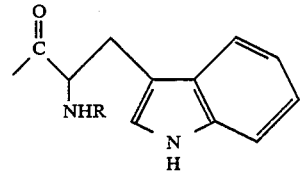

R is selected from n-decanoyl, 8-methyldecanoyl and 8-methylnonanoyl;
X is Ile or Val; and
Y is Glu or 3—MG;
provided that: (1) when X=Val and Y=3—MG, R must be 8-methyldecanoyl; and (2) when X=Val and Y=Glu, R must be 8-methylnonanoyl;
which comprises adding a C$_4$-C$_{18}$ alkyl or alkenyl alcohol, a C$_4$-C$_{18}$ alkanoic or alkenoic acid, an ester of a C$_4$-C$_{18}$ alkanoic or alkenoic acid, or a salt of a C$_4$-C$_{18}$ alkanoic or alkenoic acid, to an A54145-producing culture of *Streptomyces fradiae*, strains NRRL 18158, NRRL 18159, or NRRL 18160, or an A54145-producing mutant thereof, starting from about 20 hours to about 26 hours after initiating the production stage, and continuing throughout the fermentation until a recoverable amount of A54145 component is produced.

2. A process of claim 1 wherein a C$_4$-C$_{18}$ straight-chain alkyl or alkenyl alcohol, a C$_4$-C$_{18}$ straight-chain alkanoic or alkenoic acid, an ester of a C$_4$-C$_{18}$ straight-chain alkanoic or alkenoic acid, or a salt of a C$_4$-C$_{18}$ straight-chain alkanoic or alkenoic acid is added.

TABLE XVIII

EFFECT OF LIPID PRECURSORS ON BIOSYNTHESIS OF A54145 SIDE CHAINS IN A STIRRED 165-L BIOREACTOR

| Precursor | RQ$^a$ Calcd.$^d$ | RQ$^a$ Found$^e$ | Total A54145 (%) | Known Side Chains Percent of Total iC$_{10}$ | nC$_{10}$ | aC$_{11}$ | New Analogs$^{b,c}$ C$_6$A | C$_6$B | C$_8$A | C$_8$B | C$_9$A | C$_9$B |
|---|---|---|---|---|---|---|---|---|---|---|---|---|
| None | 1.0 | 1.0 | 100$^f$ | 76 | 14 | 10 | | | | | | |
| Acetate | 1.0 | 1.0 | 104 | 73 | 15 | 11 | | | | | | |
| Propionate | 0.88 | 0.96 | 28 | 69 | 22 | 8 | | | | | | |
| Butyrate | 0.8 | 0.93 | 49 | 28 | 58 | 15 | | | | | | |
| Hexanoate | 0.75 | 0.83 | 56 | 2 | 2 | — | 67 | 29 | | | | |
| Caprylate | 0.73 | 0.8 | 84 | 17 | 9 | 5 | | | 33 | 36 | | |
| Nonanoate | 0.72 | 0.85 | 95 | — | — | — | | | | | 75 | 25 |
| Caprate | 0.71 | 0.86 | 184 | 17 | 91 | 2 | | | | | | |
| Undecanoate | 0.76 | 0.9 | 136 | 11 | 3 | 26 | | | | | 17 | 16 |
| Undecylenate | 0.71 | 0.87 | 153 | 27 | 56 | 2 | | | | | | |
| Laurate | 0.71 | 0.9 | 154 | 43 | 54 | 3 | | | | | | |
| Tridecanoate$^g$ | 0.7 | 0.76 | 64 | 40 | 19 | 5 | | | | | 12 | 28 |
| Myristate | 0.7 | 0.81 | 207 | 10 | 85 | 5 | | | | | | |
| Oleate | 0.7 | 0.9 | 142 | 49 | 48 | 3 | | | | | | |
| Decyl Alcohol | 0.67 | 0.86 | 157 | 22 | 75 | 3 | | | | | | |

$^a$Respiration Quotient
$^b$Abbreviations as follows: "C$_6$A" = A nucleus with a C$_6$ side chain
$^c$Undecanoate and tridecanoate precursors each produced two additional unknown factors [amounts: 13 and 14% (undecanoate) and 7 and 8% (tridecanoate)]
$^d$For metabolism as sole carbon source
$^e$Represents glucose metabolism or co-metabolism with glucose
$^f$1100 mcg/mL
$^g$In 50% methyl oleate

I claim:

1. A process for preparing an A54145 component of the formula:

3. A process of claim 2 wherein n-decanoic acid, an ester of n-decanoic acid, or a salt of n-decanoic acid is added.

4. A process of claim 1 wherein a $C_4$–$C_{18}$ alkyl or alkenyl alcohol, a $C_4$–$C_{18}$ alkanoic or alkenoic acid, an ester of a $C_4$–$C_{18}$ alkanoic or alkenoic acid, or a salt of a $C_4$–$C_{18}$ alkanoic or alkenoic acid is added to the fermentation as a sterile solution.

5. A process of claim 1 wherein an ester of a $C_4$–$C_{18}$ alkanoic acid is added.

6. A process of claim 5 wherein a $C_1$–$C_4$ alkyl ester of a $C_4$–$C_{18}$ alkanoic acid is added.

7. A process of claim 6 wherein ethyl n-decanoate is added.

8. A process of claim 1 wherein a $C_4$–$C_{18}$-alkanoic acid is added.

9. A process for preparing an A54145 cyclic peptide derivative of the formula:

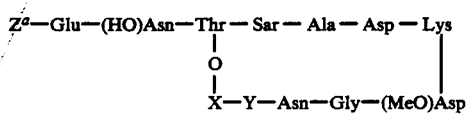

wherein
$Z^a$ is a group of formula

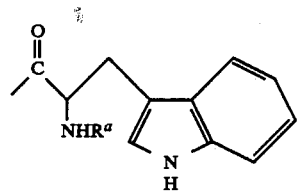

$R^a$ is $C_6$–$C_{10}$ alkanoyl;
X is Ile or Val; and
Y is Glu or 3—MG;
provided that:
(1) when X=Ile and Y=Glue or 3—MG, $R^a$ cannot be 8-methyldecanoyl, 8-methylnonanoyl, or n-decanoyl;
(2) when X=Val and Y=3—MG, $R^a$ cannot be 8-methyldecanoyl; and
(3) when X=Val and Y=Glu, $R^a$ cannot be 8-methylnonanoyl;

which comprises adding a $C_6$–$C_{10}$ alkyl or alkenyl alcohol, a $C_6$–$C_{10}$ alkanoic or alkenoic acid, an ester of a $C_6$–$C_{10}$ alkanoic or alkenoic acid, or a salt of a $C_6$–$C_{10}$ alkanoic or alkenoic acid, to an A54145-producing culture of Streptomyces fradiae, strains NRRL 18158, NRRL 18159, or NRRL 18160, or an A54145-producing mutant thereof, starting from about 20 hours to about 26 hours after initiating the production stage, and continuing throughout the fermentation until a recoverable amount of the A54145 derivative is produced.

10. A process for preparing an A54145 compound of the formula:

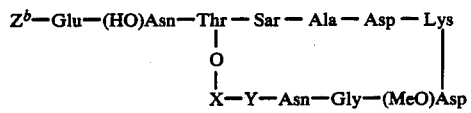

wherein $Z^b$ is a group of formula

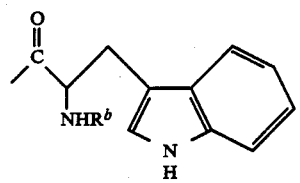

$R^b$ is $C_6$–$C_{10}$ alkanoyl;
X is Ile or Val; and
Y is a Glue or 3—MG;
which comprises feeding glucose at a rate from about 6 to about 9 grams/liter/day to an A54145-producing culture of Streptomyces fradiae, strains NRRL 18158, NRRL 18159, or NRRL 18160, or an A54145-producing mutant thereof, starting from about 18 hours to about 24 hours after initiating the production stage and continuing throughout its fermentation until a recoverable amount of an A54145 compound is produced.

11. The process of claim 10 wherein the glucose is added at a rate of about 7.5 grams/liter/day.

12. A process for preparing an A54145 compound of the formula:

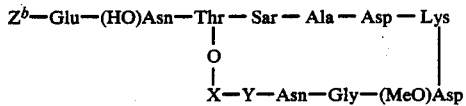

wherein
$Z^b$ is a group of formula

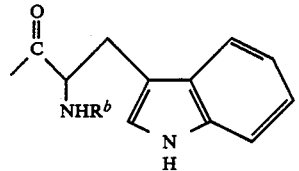

$R^b$ is $C_6$–$C_{10}$ alkanoyl;
X is Ile or Val; and
Y is Glu or 3—MG;
which comprises feeding an enzymatic soy digest at a rate from about 2 to about 4 grams/liter/day to an A54145-producing culture of Streptomyces fradiae, strains NRRL 18158, NRRL 18159, or NRRL 18160, or an A54145-producing mutant thereof, starting from about 100 hours to about 120 hours after initiating the production stage and continuing throughout its fermentation until a recoverable amount of an A54145 compound is produced.

13. The process of claim 12 wherein the soy digest is added at a rate of from about 2.5 to about 3.5 grams/liter/day.

* * * * *